United States Patent [19]

Haviv et al.

[11] 4,226,806
[45] Oct. 7, 1980

[54] 7-[(SULFOMETHYL)PHENYL-]ACETAMIDOCEPHALOSPORIN DERIVATIVES

[75] Inventors: Fortuna Haviv, Wheeling, Ill.; Abraham Patchornik, Ness Ziona, Israel

[73] Assignee: Yeda Research and Development Co. Ltd., Rehovot, Israel

[21] Appl. No.: 1,559

[22] Filed: Jan. 8, 1979

Related U.S. Application Data

[62] Division of Ser. No. 849,231, Nov. 7, 1977, Pat. No. 4,148,997.

[51] Int. Cl.$^2$ ............... C07C 143/52; C07C 143/525
[52] U.S. Cl. .................................. 260/507 R; 560/14
[58] Field of Search ....................... 260/507 R; 560/14

[56] References Cited

U.S. PATENT DOCUMENTS 3,985,739  10/1976  Dunn et al. ..................... 544/26
4,034,092   7/1977  Berges ............................ 544/26
4,057,631  11/1977  Berges ............................ 544/26
4,064,122  12/1977  Ishimaru ......................... 544/26
4,064,242  12/1977  Schmidt .......................... 544/26
4,065,619  12/1977  Morimoto et al. ............. 544/25
4,066,761   1/1978  Berges ............................ 544/26

Primary Examiner—Nicky Chan
Attorney, Agent, or Firm—Edlyn S. Simmons; L. Ruth Hattan; Eugene O. Retter

[57] ABSTRACT

Novel cephalosporin compounds of the following formula are useful as antibiotic agents:

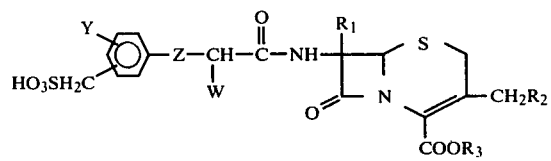

5 Claims, No Drawings

7-[(SULFOMETHYL)PHENYL]ACETAMIDOCEPHALOSPORIN DERIVATIVES

This is a division of application Ser. No. 849,231, filed Nov. 7, 1977, now U.S. Pat. No. 4,148,997.

FIELD OF INVENTION

This invention relates to novel cephalosporin derivatives useful as antibiotics and processes for their preparation.

SUMMARY OF INVENTION

Compounds of the following general Formula I are used as antibiotic agents:

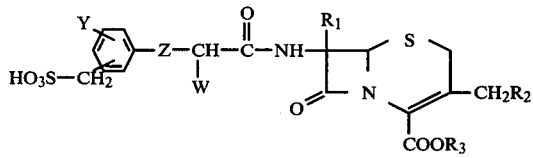

wherein Y is hydrogen, chlorine, bromine, a straight or branched lower alkyl group of from 1 to 4 carbon atoms, or an alkoxy group of from 1 to 4 carbon atoms; Z is a bond, oxygen, or sulfur; W is hydrogen, methyl, amino, hydroxy, $SO_3H$, or $COOR_4$ wherein $R_4$ is hydrogen or 5-indanyl with the proviso that when Z is oxygen or sulfur, W is other than hydroxy; $R_1$ is hydrogen or methoxy; $R_2$ is hydrogen, acetoxy, 1,3,4-thiadiazol-2-ylthio, 5-methyl-1,3,4-thiadiazol-2-ylthio, tetrazol-5-ylthio, 1-methyltetrazol-5-ylthio, 1,3,4-oxadiazol-2-ylthio, 5-methyl-1,3,4-oxadiazol-2-ylthio, 1,3,4-triazol-2-ylthio, 5-methyl-1,3,4-triazol-2-ylthio, 1,2,3-triazol-5-ylthio, pyridinium, or 4-aminocarbonylpyridinium, $R_3$ is hydrogen, a negative charge when $R_2$ is pyridinium or 4-aminocarbonylpyridinium, a cation of an alkali metal or an alkaline earth metal, ammonium or organic ammonium cations, a straight or branched lower alkyl group of from 1 to 4 carbon atoms, a straight or branched alkanoyloxymethyl group in which the alkanoyl moiety has from 2 to 5 carbon atoms and is straight or branched, an alkanoylaminomethyl group in which the alkanoyl moiety is straight or branched and has from 2 to 5 carbon atoms and the amine nitrogen may be substituted with a straight or branched lower alkyl group having 1 to 4 carbon atoms; an alkoxycarbonylaminomethyl group in which the alkoxy moiety is straight or branched and has from 1 to 4 carbon atoms and the amine nitrogen may be substituted with a straight or branched lower alkyl group of from 1 to 4 carbon atoms, a p-(alkanyoyloxy)benzyl group in which the alkanoyl moiety is straight or branched and has from 2 to 5 carbon atoms, an aminoalkanoyloxymethyl group in which the alkanoyl moiety has from 2 to 15 carbon atoms and the amino nitrogen may be mono- or di-substituted with a straight or branched lower alkyl group having from 1 to 4 carbon atoms; and pharmaceutically acceptable salts and individual optical isomers thereof.

The non-toxic acid addition salts of the compounds such as mineral acid addition salts, for example, hydrogen chloride, hydrogen bromide, hydrogen iodide, sulfate, sulfamate and phosphate and organic acid addition salts, for example maleate, acetate, citrate, oxalate, succinate, benzoate, tartrate, fumarate, malate, mandelate and ascorbate, are also included within the scope of this invention.

DETAILED DESCRIPTION OF INVENTION

In general Formula I the substituent group as represented by $R_3$ in addition to being hydrogen or a cation may also be alkanoyloxymethyl as represented by the structure:

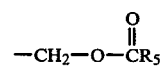

wherein $R_5$ is selected from a straight or branched lower alkyl group of from 1 to 4 carbon atoms; alkanoylaminomethyl or alkoxycarbonylaminomethyl as represented by the structure:

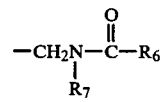

wherein $R_6$ represents a straight or branched lower alkyl group of from 1 to 4 carbon atoms or a straight or branched alkoxy group of from 1 to 4 carbon atoms, and $R_7$ is selected from hydrogen and a lower alkyl group of from 1 to 4 carbon atoms; p-(alkanoyloxy)benzyl as represented by the structure:

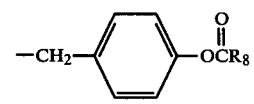

wherein $R_8$ is a straight or branched lower alkyl of from 1 to 4 carbon atoms; and aminoalkanoyloxymethyl as represented by the group:

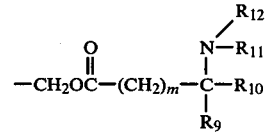

wherein m is 0 to 5, each of $R_9$ and $R_{10}$ is selected from hydrogen or lower alkyl of from 1 to 4 carbon atoms; and each of $R_{11}$ and $R_{12}$ is selected from hydrogen or a straight or branched lower alkyl group of from 1 to 4 carbon atoms.

Illustrative examples of straight or branched lower alkyl groups of from 1 to 4 carbon atoms which Y, $R_5$, $R_6$, $R_8$, $R_{11}$ and $R_{12}$ may represent are methyl, ethyl, n-propyl, isopropyl, n-butyl and tert-butyl.

Examples of lower alkyl groups of from 1 to 4 carbon atoms which $R_5$, $R_7$ and $R_8$ may represent are methyl, ethyl, n-propyl and n-butyl.

Examples of lower alkoxy groups which Y may represent are methoxy, ethoxy, n-propoxy and n-butoxy.

As used in general Formula I the terms 1,3,4-thiadiazol-2-ylthio, 5-methyl-1,3,4-thiadiazol-2-ylthio, tetrazol-5-ylthio, 1-methyltetrazol-5-ylthio, 1,3,4-oxadiazol-2-ylthio, 5-methyl-1,3,4-oxadiazol-2-ylthio, 1,3,4-triazol-2-ylthio, 5-methyl-1,3,4-triazol-2-ylthio, 1,2,3-triazol-5-ylthio, pyridinium and 4-aminopyridinium are taken to mean the following respective groups:

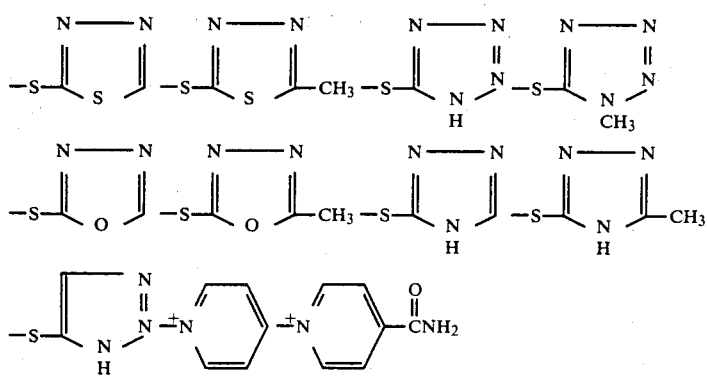

The compounds of general Formula I are prepared by coupling 7-aminocephalosporanic acid or a derivative thereof having the Formula II

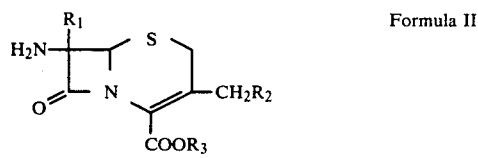

with a derivative of Formula III or a functional derivative thereof

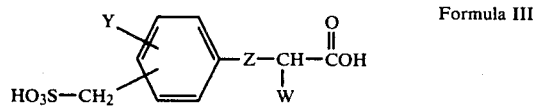

wherein $R_1$, $R_2$, $R_3$, Y, Z and W are as described in Formula I.

Functional equivalents of the acids as represented by Formula III include the acid halides, for example, the acid chloride, acid anhydrides, including mixed anhydrides with, for example, alkylphosphoric acids, lower aliphatic monoesters of carbonic acid, or alkyl or aryl sulfonic acids. Additionally, the acid azide or an active ester or thioester, for example, with p-nitrophenol, 2,4-dinitrophenol, or thioacetic acid, may be used, or the free acid as represented by Formula III may be coupled with the 7-aminocephalosporanic acid derivative as represented by Formula II after first reacting the acid with N,N'-dimethylchloroforminium chloride or by use of a carbodiimide reagent, for example, N,N'-diisopropylcarbodiimide, N,N'-dicyclohexylcarbodiimide, or N-cyclohexyl-N'-(2-morpholinoethyl)carbodiimide.

The reaction is generally carried out in the presence of a solvent, such as ethylacetate, acetone, dioxane, acetonitrile, chloroform, ethylene chloride, tetrahydrofuran or dimethylformamide and optionally in the presence of a base such as sodium bicarbonate, triethylamine or N,N-dimethylaniline. The temperature of the reaction may vary from about $-10°$ to $100°$ C., and the reaction time may vary from about ½ hour to 10 hours. The cephalosporin products are isolated by conventional methods.

The salt forms of Formula I wherein $R_3$ is a pharmaceutically acceptable cation are prepared in the manner recognized in the art and may be formed in situ or by reacting the corresponding acid with base, for example, sodium bicarbonate or triethylamine.

The compounds of general Formula II, that is, 7-aminocephalosporanic acid and 7-aminodesacetoxycephalosporanic acid and derivatives thereof are commercially available or may be obtained from Penicillin G, cephalosporin C or cephamycin C by processes known in the art. For example, compounds of Formula IV wherein $R_1$ is methoxy may be prepared as described by M. Sletzinger, et al., J. Am. Chem. Soc., 94, 1408 (1972). Compounds of Formula IV may be prepared as described in U.S. Pat. Nos. 3,948,904 and 4,026,887.

When the substituent group W in the above Formula III represents an amino group, suitable blocking groups, for example, tert-butoxycarbonyl, or carbobenzyloxy are employed to protect the amino function. Such blocking groups are removed after the coupling reaction by methods generally known in the art, for example, as described by Lemieux, et al., in U.S. Pat. No. 3,657,232.

Compounds of Formula III and the process for their preparation constitute additional aspects of this invention. The compounds of Formula III are prepared by treatment of a compound of Formula IV

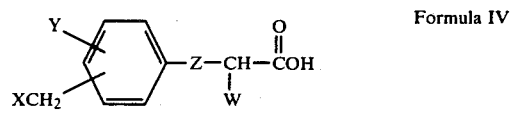

wherein Y, Z and W are as described above and X is a halogen atom such as chlorine, bromine or iodine with a compound of Formula V

wherein M is hydrogen, a cation such as sodium, potassium, ammonium or calcium and n is 1 or 2. The reaction is carried out in a suitable solvent such as water, dimethylformamide or dimethylsulfoxide. The temperature of the reaction may vary from about $-10°$ C. to $100°$ C., and the reaction time may vary from about 0.5 to 10 hours. The preferred conditions for the preparation of compounds of Formula III are the use of an equimolar mixture of a compound of Formula IV and a compound of Formula V in an aqueous medium, heating the mixture to reflux for a period of from 10 minutes to one hour and removing the solvent.

The functional derivatives of compounds of Formula III wherein the —COOH group is converted into an acid halide group may be prepared by the treatment of a compound of Formula III wherein W is other than —COOH with an acyl halide-forming reagent such as thionyl chloride, sulfuryl chloride, phosphorus pentachloride, in an inert solvent such as ether, dichloromethane or, chloroform at a temperature from 20° to 60° C. for a period of time of from 0.5 hour to 5 hours. The acyl halide product is obtained upon removal of the solvent and any excess of acyl halide-forming reagent when such is present in molar excess of compound of Formula III.

The preparation of a compound of Formula III wherein W is —COO indanyl may be carried out by reacting the corresponding compound of Formula III wherein W is —COOH with one mole of 5-indanol in an inert solvent such as chloroform, dichloromethane or, dimethylformamide, in the presence of N,N'-dicyclohexylcarbodiimide at a pH of about 2.5 and a temperature of from 20° to 30° C. The product is isolated upon filtration of the N,N'-dicyclohexylurea formed and subsequent removal of the solvent.

The compounds of Formula III are novel and are useful as intermediates for the preparation of the pharmaceutically useful cephalosporins of Formula I.

Compounds of Formula IV are described in U.S. Pat. No. 3,919,206, and the compounds of Formula V are known in the art or readily prepared by methods known in the art.

The compounds of Formula I may also be prepared by treatment of a compound of Formula VI Formula VI

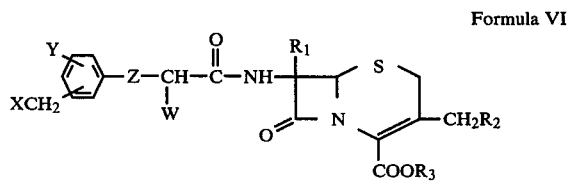

wherein Y, Z, W, $R_1$, $R_2$ and $R_3$ are as described above and X is a halogen atom such as chlorine, bromine or iodine with a compound of Formula V. The reaction is carried in a suitable solvent such as water, dimethylformamide or, dimethylsulfoxide at a temperature that may vary from 0° C. to 50° C. for from 0.5 to 10 hours. The products are isolated by conventional methods known in the art.

The pyridinium and 4-aminocarbonyl pyridinium derivatives of compounds of Formula I may also be prepared by the treatment of a derivative of Formula I wherein Y, Z, W, $R_1$ and $R_3$ are described above and $R_2$ is acetoxy, with pyridine or a suitably substituted carbamoylpyridine. The cephalosporin products are isolated by conventional methods as detailed in H. Nomura, et al., J. Med. Chem., 17, 1312 (1974).

The compounds of Formula I wherein $R_2$ is selected from a heteroarylthiol residue may also be prepared by the reaction of a compound of Formula I wherein $R_2$ is acetoxy, namely Formula VII, with an appropriate heteroarylthiol of Formula VIII as schematically described below

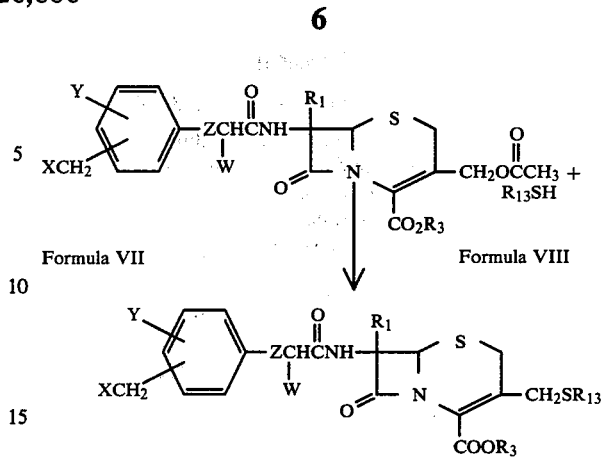

Formula VII    Formula VIII wherein X, Y, W, Z, $R_1$ and $R_3$ are as described above and $R_{13}$-S- is a heteroarylthio residue selected from 1,3,4-thiadiazol-2-ylthio, 5-methyl-1,3,4-thiadiazol-2-ylthio, tetrazol-5-ylthio, 1-methyltetrazol-5-ylthio, 1,3,4-oxadiazol-2-ylthio, 5-methyl-1,3,4-oxadiazol-2-ylthio, 1,3,4-triazol-2-ylthio, 5-methyl-1,3,4-triazol-2-ylthio and 1,2,3-triazol-5-ylthio. The reaction is generally carried out in the presence of a solvent. Suitable solvents include water, methanol, ethanol, dimethylformamide and dimethylsulfoxide. The reaction is carried out by mixing in a suitable solvent a compound of Formula VII with a compound of Formula VIII, in such a way that the compound of Formula VIII may be present in a non-stoichiometric excess relative to the compound of Formula VII. The reaction temperature may vary from about 25° C. to 100° C., and the reaction time may vary from about 0.5 hour to 10 hours. The reaction may be carried out in the presence of a base such as sodium carbonate, sodium bicarbonate or triethylamine. The product of the reaction is isolated by conventional methods known in the art.

The individual optical isomers of the compounds of general Formula I wherein W represents methyl, amino, hydroxy, COOH or $SO_3H$ are also included within the scope of this invention.

The novel compounds of this invention are useful as antibiotic agents as demonstrated by their activity against gram positive and gram negative bacteria in vitro and in vivo and against fungi. The compounds of this invention are particularly useful in that they possess a longer duration of activity than many of the well known cephalosporin compounds. Illustrative examples of bacteria against which the compounds of this invention are active are *Staphylococcus aureus, Salmonella schottmulleri, Klebsiella pneumoniae, Diplococcus pneumonia* and *Streptococcus pyogenes.*

The compounds of this invention may be administered alone or in the form of pharmaceutical preparations either orally, parenterally or topically. They may be administered to warm blooded animals, that is, birds and mammals, for example felines, canines, bovines, and equines, and humans. For oral administration the compounds may be administered in the form of tablets, capsules or pills or in the form of elixirs or suspensions. For parenteral administration they are best used in the form of a sterile aqueous solution which may contain other solutes, for example, enough saline or glucose to make the solution isotonic. For topical administration the compounds may be incorporated into creams or ointments.

EXAMPLE 1 p-Sulfomethylphenylacetic Acid

To a boiling aqueous solution of sodium bisulfite (1.47 g, 0.0141 mole) is added in portions p-chloromethylphenylacetic acid (2.6 g, 0.0141 mole). The solution is further refluxed for 30 minutes and is then evaporated to dryness to give a quantitative yield of the title compound.

NMR (DMSO-$D_6$) ppm ($\delta$) 3.57 (s,2) 4.50 (s,2), 7.28 (s,4).

EXAMPLE 2 p-Sulfomethylphenylacetyl Chloride

To a solution of thionyl chloride in 20 ml of anhydrous ether is added p-sulfomethylphenylacetic acid. The mixture is stirred at room temperature until gas evolution ceases. Two drops of dimethylformamide is added, and the resulting mixture is stirred at 40° C. for 2.5 hours. The title compound is obtained after filtration and evaporation of the reaction mixture. The infrared spectrum of the product shows a characteristic acid chloride absorption at 1830 cm$^{-1}$ whereas the starting acid shows a carbonyl absorption at 1740 cm$^{-1}$.

When in Example 1 an acid selected from Table I is substituted for chloromethylphenylacetic acid the respective sulfomethyl derivative of Formula III listed in Table I is obtained, which can be converted into the corresponding acid chlorine when treated as described in Example 2.

TABLE 1

| ACID DERIVATIVE | PRODUCT |
| --- | --- |
| 2-sulfo-p-chloromethyl-phenylacetic acid | 2-sulfo-p-sulfomethyl-phenylacetic acid |
| 2-(p-chloromethylphenyl)-malonic acid | 2-(p-sulfomethylphenyl)-malonic acid |
| p-chloromethylphenyl-glycine | p-sulfomethylphenyl-glycine |
| p-chloromethylmandelic acid | p-sulfomethylmandelic acid |
| p-chloromethylphenoxy-acetic acid | p-sulfomethylphenoxy-acetic acid |
| p-chloromethylphenyl-acetic acid | p-sulfomethylphenyl-acetic acid |
| p-chloromethylthiophen-oxyacetic acid | p-sulfomethylthiophen-oxyacetic acid |

GENERAL PROCEDURE FOR THE PREPARATION OF p-SULFOMETHYLPHENYLACETAMIDOCEPHALOSPORIN DERIVATIVES

To a solution of an appropriate derivative of Formula II (1 equivalent) and sodium bicarbonate (3.5 equivalents) in water at 0°–5° C. is added a solution of the product obtained according to Example 2 in acetone. The mixture is stirred at 0°–5° C. for 30 minutes and at about 25° C. for 1 hour. The acetone is evaporated, the pH of the aqueous phase is adjusted to 4.5, and the mixture is filtered. The filtrate is then further acidified to pH 2 to give the desired product as a solid which is filtered and dried.

EXAMPLE 3

3-[(Acetyloxy)methyl]-8-oxo-7-[[[4-(sulfomethyl)-phenyl]acetyl]amino]-5-thia-1-azabicyclo[4.2.0]oct-2-ene-2-carboxylic acid The title compound is obtained in 39% yield when prepared according to the above general procedure from 7-aminocephalosporanic acid (a compound of Formula II) and p-sulfomethylphenylacetyl chloride (a compound of Formula III). NMR (DMSO-$D_6$+$D_2$O) ppm ($\delta$) 2.03 (s,3) 3.3–3.9 (superimposed q,2 and s,2) 4.6–5.2 (superimposed m,2; s,2 and d,1), 6.6 (d,1), 6.6 (d,1), 7.4 (s,4).

When in the procedure of Example 3 an appropriate amount of a cephalosporin derivative of Formula II, listed in the following Table II is substituted for 7-aminocephalosporanic acid and is treated with an appropriate amount of acid chloride of a compound of Formula III listed in Table I the respective 7-[[(sulfomethyl)phenyl]acetamido]cephalosporin products listed in Table II are obtained.

TABLE II

| ACID | 7-AMINOCEPHALOSPORANIC-ACID DERIVATIVE | PRODUCT |
| --- | --- | --- |
| p-sulfomethylphenyl-acetic acid | 3-[(1-methyltetrazol-5-ylthio)-methyl]-7-amino-8-oxo-5-thia-1-azabicyclo[4.2.0]oct-2-ene-2-carboxylic acid pivalyloxymethyl ester | 3-[[(1-methyl-1H-tetrazol-5-yl)-thio]methyl]-8-oxo-[[[4-(sulfomethyl)phenyl]acetyl]amino]-5-thia-1-azabicyclo[4.2.0]oct-2-ene-2-carboxylic acid, (2,2-dimethyl-1-oxopropoxy)methyl ester |
| p-sulfomethylmandelic acid | 3-[(2-methyl-1,3,4-thiadiazole-5-ylthio)methyl]-7-amino-8-oxo-5-thia-1-azabicyclo[4.2.0]oct-2-ene-2-carboxylic acid | 7-[[Hydroxy[4-(sulfomethyl)-phenyl]acetyl]amino]-3-[[(5-methyl-1,3,4-thiadiazol-2-yl)-thio]methyl]-8-oxo-5-thia-1-azabicyclo[4.2.0]oct-2-ene-2-carboxylic acid |
| 2-sulfo-p-sulfomethyl-phenylacetic acid | 3-[(acetyloxy)methyl]-7-amino-8-oxo-5-thia-1-azabicyclo-[4.2.0]oct-2-ene-2-carboxylic acid | 3-[(acetyloxy)methyl]-8-oxo-7-[[sulfo[4-(sulfomethyl)phenyl]-acetyl]amino]-5-thia-1-azabi-cyclo[4.2.0]oct-2-ene-2-carbox-ylic acid |
| p-sulfomethylphenyl-glycine | 7-amino-3-methyl-8-oxo-5-thia-1-azabicyclo[4.2.0]oct-2-ene-2-carboxylic acid | 7[[amino[4-(sulfomethyl)phenyl]-acetyl]amino]-3-methyl-8-oxo-5-thia-1-azabicyclo[4.2.0]oct-2-ene-2-carboxylic acid |
| 2-(p-sulfomethyl-phenyl)malonic acid | 3-[1-methyltetrazol-5-ylthio)-methyl]-7-amino-8-oxo-5-thia-1-azabicyclo[4.2.0]oct-2-ene-2-carboxylic acid | 7-[[carboxy[4-(sulfomethyl)-phenyl]acetyl]amino]-3-[[(1-methyl-1H-tetrazol-5-yl)thio]-methyl]-8-oxo-5-thia-1-azabi-cyclo[4.2.0]oct-2-ene-2-carbox- |

| ACID | 7-AMINOCEPHALOSPORANIC-ACID DERIVATIVE | PRODUCT |
|---|---|---|
| p-sulfomethylphenoxy-acetic acid | 3-[(acetyloxy)methyl]-7-amino-8-oxo-5-thia-1-azabicyclo[4.2.0]-oct-2-ene-2-carboxylic acid | ylic acid 3-[(acetyloxy)methyl]-7-[[[4-(sulfomethyl)phenoxy]acetyl]-amino]-8-oxo-5-thia-1-azabicyclo-[4.2.0]oct-2-ene-2-carboxylic acid |

EXAMPLE 4

3-[[(1-Methyl-1H-tetrazol-5-yl)thio]methyl]-8-oxo-7-[[[4-(sulfomethyl)phenyl]acetyl]amino]-5-thia-1-azabicyclo[4.2.0]oct-2-ene-2-carboxylic acid.

The title compound is obtained in 23% yield when prepared according to the general procedure from 3-(1-methyltetrazoyl-5-thio methyl)-7-amino-8-oxo-5-thia-1-azabicyclo[4.2.0]oct-2-ene-2-carboxylic acid (a compound of Formula II) and p-sulfomethylphenylacetyl chloride (a compound of Formula III).

NMR (DMSO-D$_6$+D$_2$O) ppm (δ) 3.6 (broad, s,2), 3.87 (s,2), 4.0 (s,3), 4.2 (broad s,2), 4.75 (s,2), 5.1 (d,1), 5.7 (d,1), 7.2–7.4 (m,4).

EXAMPLE 5

3-[[(5-Methyl-1,3,4-thiadiazol-2-yl)thio]methyl]-8-oxo-7-[[[4-(sulfomethyl)phenyl]acetyl]amino]-5-thia-1-azabicyclo[4.2.0]oct-2-ene-2-carboxylic acid.

The title compound is obtained in 53% yield when prepared according to the general procedure from 3-(5-methyl-1,3,4-thiadiazolyl-2-thio methyl)-7-amino-8-oxo-5-thia-1-azabicyclo[4.2.0]oct-2-ene-2-carboxylic acid (a compound of Formula II) and p-sulfomethylphenylacetyl chloride (a compound of Formula III).

NMR (DMSO-D$_6$+D$_2$O) 2.70 (s,3) 3.4–3.8 (superimposed, s,2 and m,2), 4.75 (s,2), 5.1 (d,1), 5.7 (d,1), 7.1–7.6 (m,4).

We claim:

1. A compound of the formula

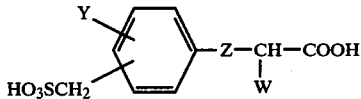

wherein Y is hydrogen, chlorine, bromine, a straight or branched lower alkyl group of from 1 to 4 carbon atoms, or an alkoxy group of from 1 to 4 carbon atoms, Z is a bond, oxygen or sulfur; W is selected from hydrogen, methyl, amino, hydroxy, SO$_3$H, or COOR$_4$ wherein R$_4$ is selected from hydrogen or 5-indanyl with the proviso that when Z is oxygen or sulfur, W is other than hydroxy, or an acid halide thereof, with the proviso that when the compound is the acid halide, W is other than COOH.

2. A compound of the formula

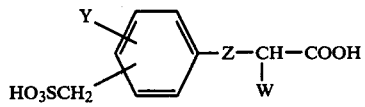

wherein Y is hydrogen, chlorine, bromine, a straight or branched lower alkyl group of from 1 to 4 carbon atoms, or an alkoxy group of from 1 to 4 carbon atoms, Z is a bond, oxygen or sulfur; W is selected from hydrogen, methyl, amino, hydroxy, SO$_3$H, or COOR$_4$ wherein R$_4$ is selected from hydrogen or 5-indanyl with the proviso that when Z is oxygen or sulfur, W is other than hydroxy.

3. A compound of claim 2 wherein Z is a bond.

4. A compound of claim 2 which is p-sulfomethylphenylacetic acid.

5. A compound of claim 1 which is p-sulfomethylphenylacetyl chloride.

* * * * *